US00PP11039P

United States Patent [19]

Cunneen

[11] Patent Number: Plant 11,039

[45] Date of Patent: Aug. 24, 1999

[54] ARGYRANTHEMUM PLANT NAMES 'SUMMER PINK'

[75] Inventor: Thomas Michael Cunneen, Theresa Park, Australia

[73] Assignee: University of Sydney Plant Breeding Institute, Cobbitty, Cobbitty, Australia

[21] Appl. No.: 08/939,427

[22] Filed: Sep. 26, 1997

[51] Int. Cl.[6] ..... A01H 5/00

[52] U.S. Cl. ..... Plt./263

[58] Field of Search ..... Plt./68.1, 82.1, Plt./263

*Primary Examiner*—Howard J. Locker
*Assistant Examiner*—Melissa L. Kimball
*Attorney, Agent, or Firm*—C. A. Whealy

[57] ABSTRACT

A distinct cultivar of Marguerite Daisy plant named Summer Pink, characterized by its upright, uniform and open plant habit; freely branching plant form; numerous inflorescences per plant; early flowering; large daisy-type inflorescences; and soft pink ray florets and bright yellow disc florets.

1 Drawing Sheet

The present invention relates to a new and distinct cultivar of Marguerite Daisy plant, botanically known as *Argyranthemum frutescens* and referred to by the cultivar name Summer Pink.

The new cultivar is a product of a planned breeding program conducted by the inventor in Cobbitty, New South Wales, Australia. The objective of the breeding program was to develop compact and freely-flowering Marguerite daisies that have large inflorescences with good form.

The new cultivar originated from a cross made by the inventor in 1992 of the *Argyranthemum frutescens* cultivar (not patented) Canary Island Daisy, as the male or pollen parent, with the *Argyranthemum frutescens* cultivar Dolly (not patented), as the female or seed parent. The cultivar Summer Pink was discovered and selected by the inventor as a flowering plant within the progeny of the stated cross in a controlled environment in Cobbitty, New South Wales, Australia. Compared to plants of the male parent, the cultivar Canary Island Daisy, plants of the new Marguerite Daisy are taller and have larger inflorescences. In addition, leaves of plants of the new Marguerite Daisy are greener and ray floret color is different than plants of the cultivar Canary Island Daisy. Compared to plants of the female parent, the cultivar Dolly, plants of the new Marguerite Daisy are more compact and have larger inflorescences.

Asexual reproduction of the new cultivar by terminal cuttings taken in Macquarie Fields and Cobbitty, New South Wales, Australia, has shown that the unique features of this new Marguerite Daisy are stable and are reproduced true to type in successive propagations.

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Summer Pink' which distinguish 'Summer Pink' as a new and distinct cultivar:

1. Upright, uniform and open plant habit.
2. Freely branching plant form.
3. Numerous inflorescences per plant.
4. Early flowering.
5. Large daisy-type inflorescences.
6. Soft pink ray florets and bright yellow disc florets.

Plants of the new Marguerite Daisy can be compared to plants of the cultivar Single Pink (not patented). In side-by-side comparisons conducted in Cobbitty, New South Wales, Australia, plants of the new Marguerite Daisy had a more intense pink ray floret color, were more compact and had narrower and shorter leaves.

BRIEF DESCRIPTION OF THE PHOTOGRAPHS

The accompanying colored photograph illustrate the overall appearance of the new cultivar, showing the colors as true as it is reasonably possible to obtain in colored reproductions of this type.

The photograph at the top of the sheet comprises a side perspective view of a typical container plant of 'Summer Pink'. The photograph at the bottom of the sheet comprises a close-up view of typical inflorescences and leaves of 'Summer Pink'. Floret and foliage colors in the photographs may appear different from the actual colors due to light reflectance.

DETAILED BOTANICAL DESCRIPTION

The following observations, measurements and values describe plants grown in Encinitas, Calif., in a polyethylene-covered greenhouse with day and night temperatures averaging 24 and 15° C., respectively. Color references are made to The Royal Horticultural Society Colour Chart except where general terms of ordinary dictionary significance are used.

Botanical Classification: *Argyranthemum frutescens* cultivar Summer Pink.

Parentage:

*Male or pollen parent.*—*Argyranthemum frutescens* cultivar Canary Island Daisy (not patented).

*Female or seed parent.*—*Argyranthemum frutescens* cultivar Dolly (not patented).

Propagation:

*Type cutting.*—Terminal cuttings.

*Time to initiate and develop roots.*—About 10 or 14 days at temperatures of 26 or 18° C., respectively.

*Rooting habit.*—Numerous, fibrous, and freely branching.

Plant description:

*General appearance.*—Upright, inverted triangle, uniform, but open habit. Herbaceous plant with pinnatifid foliage and erect flower stems that hold the inflorescences above the foliage. Appropriate for various sizes and types of containers.

*Plant height.*—About 36 cm from soil level to top of inflorescences.

*Plant width.*—About 32 cm.

*Branching.*—Freely branching, plants usually do not require pinching.

*Vigor.*—Moderately vigorous.

*Internode length.*—About 1.4 cm.

*Stem color.*—143C.

*Foliage description.*—Arrangement: Alternate, single. Shape: Pinnatifid. Apex: Acute. Base: Attenuate, sessile. Margin: Deeply incised. Length: About 8 cm. Width: About 4.5 cm. Texture: Glabrous and smooth. Durability to stresses: Good. Color: Young leaves, upper surface: 143B. Young leaves, lower surface: 143C. Mature leaves, upper surface: 137B. Mature leaves, lower surface: 137C. Venation, upper surface: 137B. Venation, lower surface: 137C.

Flowering description:

*Flowering habit.*—Single daisy-type composite inflorescence form. Inflorescences form at upper leaf axils. Florets arranged acropetally on a capitulum. Inflorescences last about four or five days.

*Quantity of inflorescences.*—Freely flowering, typically 5 to 6 flowers per lateral stem. About 30 inflorescences in flower per plant.

*Natural flowering season.*—Natural flowering season is spring to early fall. Plants flower continuously during this period.

*Inflorescence diameter.*—About 4.6 cm.

*Inflorescence depth* (*height*).—About 1 cm.

*Fragrance.*—None.

*Ray florets.*—Appearance: Satiny. Aspect: Flat. Shape: Elliptic. Apex: Tri-dentate. Base: Attenuate. Margin: Entire. Length: About 2.2 cm. Width: About 7 mm. Texture: Smooth, glabrous. Color: When opening, upper surface: 155B. When opening, lower surface: 155A. Mature, upper surface: 73C, floret color fades to 75C with subsequent development. Mature, lower surface: 73D. Number of ray florets per inflorescence: About 16 in one whorl.

*Disc florets.*—Shape: Tubular, 5-parted and flared at apex. Diameter of disc: About 1.2 cm. Disc floret length: About 3 mm. Disc floret width: About 1 mm. Color: Immature: 12A. Mature: 13A at apex, 12C tube. Number of disc florets per inflorescence: Numerous.

*Phyllaries.*—Arrangement: Overlapping in alternate rows, tightly pressed to the receptacle. Length: About 6 mm. Diameter: About 1 mm. Shape: Elliptic.

*Peduncle.*—Length: First peduncle: About 13 cm. Fourth peduncle: About 16 cm. Strength: Moderate to strong and erect, inflorescences held above foliage. Texture: Smooth. Color: 138B.

*Flower bud.*—Shape: Spherical. Length: About 8 mm. Diameter: About 7 mm. Color: 145D.

*Androecium.*—Present on disc florets only. Anther color: 13A. Pollen color: 13A. Amount of pollen: Moderate.

*Gynoecium.*—Present on ray and disc florets. Pistil number: One per floret. Pistil length: About 3 mm. Style length: About 2.5 mm. Style color: 1C. Stigma shape: Bipartate. Stigma color: 14A. Ovary color: 1C.

Disease resistance: No resistance to fungal, bacterial or viral pathogens has been noted.

Seed production: Seed production is typically not observed.

It is claimed:

1. A new and distinct Marguerite Daisy plant named 'Summer Pink', as illustrated and described.

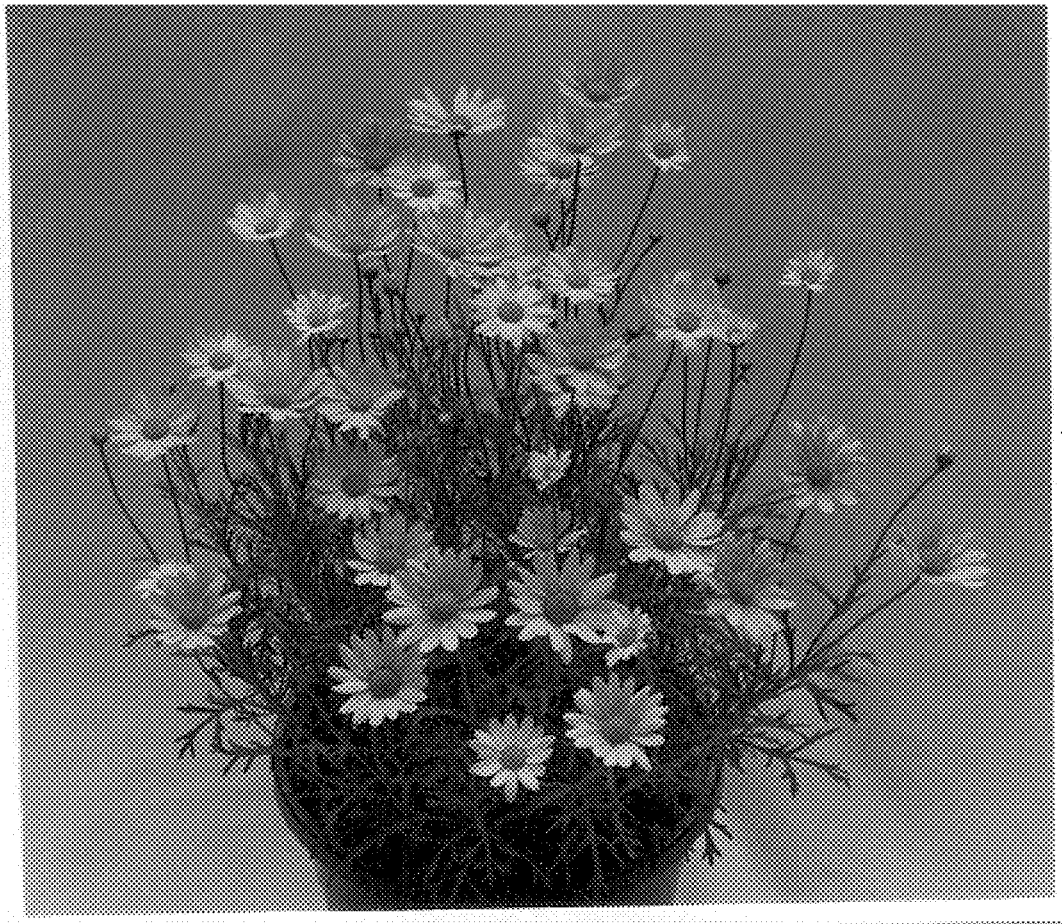
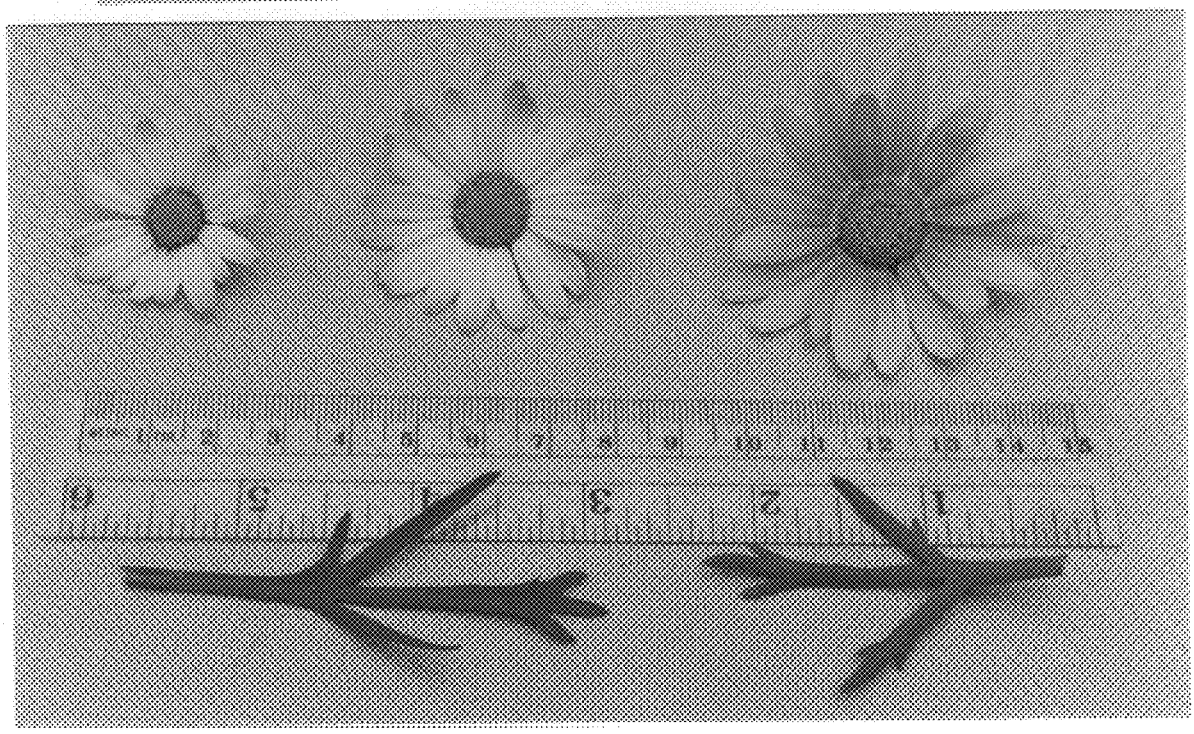

* * * * *